United States Patent [19]
Benson et al.

[11] Patent Number: 5,679,684
[45] Date of Patent: Oct. 21, 1997

[54] HYDROXYALKYLAMMONIUM-PYRIMIDINES AND NUCLEOSIDE DERIVATIVES, USEFUL AS INHIBITORS OF INFLAMMATORY CYTOKINES

[75] Inventors: Bradley J. Benson, Chapel Hill, N.C.; Xiannong Chen, Athens, Ga.; George J. Cianciolo, Chapel Hill, N.C.; Jose-Luis Diaz, Durham, N.C.; Khalid S. Ishaq, Chapel Hill, N.C.; Susan L. Morris-Natschke, Apex, N.C.; Ronald J. Uhing, Durham, N.C.; Henry Wong, Morrisville, N.C.

[73] Assignees: Macronex, Inc.; The University of N.C. at Chapel Hill, both of Morrisville, N.C.

[21] Appl. No.: 476,704

[22] Filed: Jun. 7, 1995

Related U.S. Application Data

[62] Division of Ser. No. 264,026, Jun. 22, 1994, Pat. No. 5,550,132.

[51] Int. Cl.$^6$ .................................................. A61K 31/505
[52] U.S. Cl. ........................... 514/269; 514/50; 514/274
[58] Field of Search ........................ 514/50, 269, 274

[56] References Cited

U.S. PATENT DOCUMENTS

| | | | |
|---|---|---|---|
| 4,199,574 | 4/1980 | Schaeffer | 544/276 |
| 5,130,302 | 7/1992 | Spielvogel et al. | 514/45 |
| 5,306,722 | 4/1994 | Kim et al. | 514/274 |
| 5,306,732 | 4/1994 | Norris et al. | 514/729 |

FOREIGN PATENT DOCUMENTS

| | | | |
|---|---|---|---|
| 0181075 | 9/1985 | Japan | 544/312 |
| WO 92/17186 | 10/1992 | WIPO | |
| WO 94/01413 | 1/1994 | WIPO | |

OTHER PUBLICATIONS

CA 109:38194, 1988.
Parmely et al. (1993) "Adenosine and a related carbocyclic nucleoside analogue selectively inhibit tumor necrosis factor–alpha production and protect mice against endotoxin challenge" J. Immunol. 151:389–96.

Ruddle et al., 1990, "An antibody to lymphotoxin and tumor necrosis factor prevents transfer of experimental allergic encephalomyelitis" J. Exp. Med. 172:1193–1200.

Sood et al., 1992, "The synthesis and antineoplastic activity of 2'–deoxynucleoside–cyanoboranes in murine and human culture cells" Anticancer Research 12:335–44.

Sood et al., 1990, "Boron–containing nucleic acids. 2. Synthesis of oligonucleoside boranophosphates" J. Am. Chem. Soc. 112:9000–1.

Sood et al., 1989, "Boron–containing nucleic acids. 2. Synthesis of cyanoborane adducts of 2'deoxy–ucleosides" J. Am. Chem. Soc. 111:9234–5.

Spielvogel et al., 1991, "From boron analogues of amino acids to boronated DNA:potential new pharmaceuticals and neutron capture agents" Pure & Appl. Chem. 63:415–8.

Kolb et al. (1985) "Synthesis of 5'-[(3-Aminooxypropyl)amino]-5'-deoxyadenosine" Liebigs Annalen Der Chemie No.5:1036–40.

Lee et al. (1994) "Low–molecular–weight TNF biosynthesis inhibitors: strategies and prospectives" Circulatory Shock 44:97–103.

*Primary Examiner*—Yogendra N. Gupta
*Attorney, Agent, or Firm*—Klauber & Jackson

[57] ABSTRACT

Novel hydroxyalkylammonium-pyrimidine of the formula

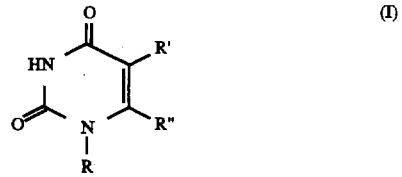

(I)

and nucleoside derivatives have been found to be useful as inhibitors of inflammatory cytokines. They can be used, inter alia, in the therapy of septic shock, cachexia, rheumatoid arthritis, inflammatory bowel disease, multiple sclerosis and AIDS. The compounds are typically prepared by reaction of an iodo substituted nucleoside with the appropriately substituted hydroxyalkylamine.

25 Claims, No Drawings

HYDROXYALKYLAMMONIUM-PYRIMIDINES AND NUCLEOSIDE DERIVATIVES, USEFUL AS INHIBITORS OF INFLAMMATORY CYTOKINES

This application is a division of application Ser. No. 08/264,026 filed Jun. 22, 1994 now U.S. Pat. No. 5,550,132.

BACKGROUND OF THE INVENTION

Tumor necrosis factor alpha (TNF-α), also known as cachectin, is a 17 kDa protein produced by neutrophils, activated lymphocytes, macrophages, NK cells, LAK cells, astrocytes, endothelial cells, smooth muscle cells, and some transformed cells. A large number of studies reveal that TNF-α is produced principally by macrophages and that it may be produced in vitro as well as in vivo. This cytokine mediates a wide variety of biological activities, including: cytotoxic effects against tumor cells, activation of neutrophils, growth proliferation of normal cells, and immunoinflammatory, immunoregulatory, and antiviral responses. TNF-α also induces the secretion of interleukin-1 (In-1) and is a primary mediator of inflammation and endotoxin-induced shock. A 26 kDa membrane form of TNF-α has been described on the surface of monocytes and activated T cells. This molecule may be involved in intracellular communication, as well as cytotoxic activity, and is a surface marker for lymphocyte activation. By a variety of techniques TNF has been shown to exist as a trimer in aqueous solutions; only a small fraction of human TNF molecules occur as monomers at physiological ionic pH.

Two distinct TNF-α receptors have been identified: a 75 kDa receptor and a 55 kDa receptor, TNFR-α and TNFR-β respectively. The intracellular domains of the two TNF receptor types are apparently unrelated, suggesting that they employ different signal transduction pathways. While both receptors are capable of binding TNF and activating the transcription factor NFkB, it appears that the expression of each receptor is independently and differentially regulated. Human TNF-α will bind to both types of receptors with equal affinity on human cells.

TNF has been found to be an important mediator of the pathophysiological effects of a diverse array of invasive diseases, infections, and inflammatory states. As a consequence of its production (or overproduction) in tissues, and the presence of other cytokines in the cellular environment, TNF may ultimately benefit or injure the host. For instance, when produced acutely and released in large quantities into the circulation during a serious bacterial infection, it triggers a state of shock and tissue injury (septic shock syndrome) that carries an extremely high mortality rate (30 to 90%). Three main lines of evidence indicates that TNF plays a central role in the development of septic shock: (1) administration of the cytokine to mammals induces a state of shock and tissue injury that is nearly indistinguishable from septic shock; (2) inhibiting TNF in septic shock prevents the development of both shock and tissue injury and confers a significant survival advantage; and (3) TNF is produced in animals and humans during experimental and clinical septic shock syndrome.

When produced during chronic disease states, TNF mediates cachexia, a syndrome characterized by anorexia, accelerated catabolism, weight loss, anemia, and depletion of body tissues. Weight loss frequently develops during chronic illness and, if not reversed, may kill the host before the underlying disease can be eradicated. For instance, it is not unusual for the patient afflicted with cancer of AIDS to lose 50% of body weight and to succumb to complications of malnutrition. By contrast to starvation, during which protein-conserving adaptive responses are maximally operative, the cachectic host tends to catabolize body energy stores in the face of suppressed intake, thus hastening its own demise.

In addition to septic shock and cachexia, TNF has been implicated in the pathophysiology of rheumatoid arthritis (RA), inflammatory bowel disease (IBD), multiple sclerosis (MS) and AIDS and has been suggested to perhaps play a role in the development of Alzheimer's disease (AD) and/or the weight loss associated with AD patients. In rheumatoid arthritis, for instance, there is evidence of macrophage activation with demonstration of increased amounts of two monokines, TNF-α and IL-1, in the serum but even more in the synovial fluid. TNF-α, an inducer of IL-1, is significantly elevated in rheumatoid arthritis but not in reactive arthritis. Moreover, TNF-α levels in RA correlate with the synovial fluid leukocyte count and with the ESR (erythrocyte sedimentation rate). TNF is an important mediator of immunity and inflammation and because of its biologic activities (activation of neutrophils, release of arachidonic acid metabolites from synovial cells, induction of cartilage resorption and inhibition of proteoglycan release in cartilage, induction of macrophage chemotactic activating protein ([MCAP]) is one of the potential mediators in chronic arthritis. Studies have shown that monoclonal antibody to TNF can ameliorate joint disease in murine collagen-induced arthritis. In these studies, anti-TNF administered prior to the onset of disease significantly reduced paw swelling and histological severity of arthritis without reducing the incidence of arthritis or the level of circulating anti-type II collagen IgG. More relevant to human disease was the ability of the antibody to reduce the clinical score, paw swelling, and the histological severity of disease even when injected after the onset of clinical arthritis.

More recently, 20 patients with active rheumatoid arthritis were treated with 20 mg/kg of chimeric human/mouse monoclonal anti-TNF-α in an open phase I/II trial lasting eight weeks. The treatment was, well-tolerated and significant improvements were seen in the Ritchie Articular Index, the swollen joint count, and in other major clinical assessments. Significant decreases were seen in serum amyloid A, IL-6 and c-reactive protein.

Multiple sclerosis (MS) is a chronic, inflammatory, demyelinating disease of the central nervous system (CNS). The majority of infiltrating cells at the site of demyelination are macrophages and T-cells. IL-1 and TNF in the CSF are detected at higher levels and more frequently in patients with active multiple sclerosis than in patients with inactive MS or with other neurological diseases. In a study of MS patients, Beck and colleagues found an increase of TNF and interferon production by peripheral blood mononuclear cells two weeks prior to disease exacerbation. Experimental allergic encephalomyelitis (EAE) is the best characterized demyelinating disease of the CNS in animals. EAE and MS share many characteristics. Ruddle and colleagues used a monoclonal antibody which neutralizes TNF to treat EAE in mice. See Ruddle et al., *J. Exp. Med.*, 1990, 172:1193–1200. The incidence and severity of EAE in the antibody-treated mice were dramatically reduced and the onset of disease was delayed. Moreover, the authors reported that the preventive therapy was long-lived, extending through five months of observation.

TNF-α levels were measured in serum samples from 73 HIV-1 seropositive patients and in samples from two control groups. All clinical groups of HIV-1-infected patients, regardless of concurrent illness, had significantly elevated levels of both types of soluble TNF receptors (sTNFRs) and immunoreactive TNF-α, with the highest concentrations among the AIDS patients. These TNF parameters were significantly correlated with reduced CD4+ lymphocyte counts. The raised levels of immunoreactive TNF and sTN-FRs strongly indicate activation of the TNF-α system during HIV-1 infection. Levels increase with disease progression and degree of immunodeficiency. Thalidomide, a selective inhibitor of TNF-α synthesis, has been shown to suppress the activation of latent HIV-1 in a monocytoid (U1) cell line. Associated with HIV-1 inhibition was a reduction in agonist-induced TNF-α protein and mRNA production. The presence of thalidomide was also shown to inhibit the activation of virus in the peripheral blood mononuclear cells of 16 out of 17 patients with advanced HIV-1 infection and AIDS. A recent study used reverse transcriptase-polymerase chain reaction on homogenized brain tissue to correlate the relative expression of mRNA for TNF-α with cognitive impairment and with neuropathologic changes in HIV infected patients. Levels of mRNA for TNF-α from frontal subcortical white matter were significantly greater in patients with HIVD (HIV associated dementia) than in AIDS patients without dementia or in seronegative controls. Elevated levels of mRNA for TNF-α in HIVD indicate that abnormal cytokine expression may contribute to the pathogenesis of HIVD. Pentoxifylline (PTX), a drug known to block TNF-α release, was tested in a phase I/II clinical trial of HIV-seropositive patients either alone or in combination with zidovudine (ZDV). The mean HIV-1 viral load, as measured by a quantitative polymerase chain reaction technique, was 1.9-fold above baseline values after 12 weeks of PTX and ZDV compared with 8- to 9-fold greater levels in patients given either agent alone (p<0.05). TNF-α levels correlated with viral load (p<0.0001) in patients given the combined drug regimen. Crohn's disease and ulcerative colitis are chronic inflammatory bowel diseases of unknown etiology but there is circumstantial evidence that immune mechanisms play an important role in the pathogenesis of the intestinal lesion and that cytokines produced by lymphoid cells may be critical for the extraintestinal sequelae of the disease. In both Crohn's disease and ulcerative colitis, activation of macrophages seems to be a key feature and increased production of the macrophage-derived cytokines TNF-α, IL-1, and IL-6 have been reported in both diseases. A recent study determined the location and tissue density of cells immunoreactive for TNF-α in intestinal specimens from 24 patients with chronic inflammatory bowel disease (15 with Crohn's, 9 with ulcerative colitis) and 11 controls (14). There was significantly increased density of TNF-α immunoreactive cells in the lamina propria of both ulcerative colitis and Crohn's disease specimens suggesting that this degree of TNF-α production probably contributes significantly to the pathogenesis of both Crohn's disease and ulcerative colitis by impairing the integrity of epithelial and endothelial membranes, increasing inflammatory cell recruitment, and by prothrombotic effects on the vascular endothelium.

SUMMARY OF THE INVENTION

The present invention relates to novel hydroxy alkylammonium-pyrimidines or purines and nucleoside derivatives which are particularly useful as inhibitors of inflammatory cytokines such as IL-1b, IL-6, IL-8, TNFα and tissue factor. More particularly, the present invention relates to novel inhibitors of inflammatory cytokines which are compounds of the Formulae I

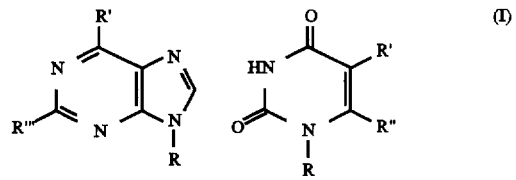

wherein R is a group of the formula

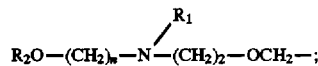

wherein $R_1$ is one or two lower alkyl groups with the proviso that when two lower alkyl groups are present, then the nitrogen atom is quarternized; $R_2$ is hydrogen or a saturated or unsaturated alkanoyl group of 2–20 carbon atoms; n is 2–6; or R is a substituted furanyl group of the formula

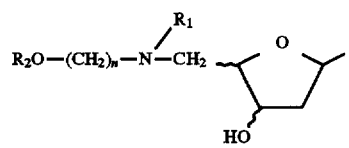

wherein n, $R_1$ and $R_2$ are as hereinbefore defined; and the wavy lines indicate either stereochemical configuration; R' and R" are independently hydrogen, halogen or a lower alkyl, lower alkenyl, lower alkynyl, or aralkyl group; R''' is hydrogen, halogen, alkylthio, amino, acylamino carbamyl or azide; and the pharmaceutically acceptable salts thereof.

It is thus an object of the present invention to provide hydroxyalkylammonium-pyrimidines or purines and nucleosides which, by virtue of their ability to inhibit inflammatory cytokines, are useful as therapeutic agents for the treatment of invasive diseases, infections and inflammatory states, particularly septic shock, cachexia, rheumatoid arthritis, inflammatory bowel disease, multiple sclerosis, AIDS and Alzheimer's disease.

It is further an object of the present invention to provide synthetic procedures for the preparation of the novel hydroxyalkylammonium-pyrimidines or purines and nucleosides.

It is a still further object of the present invention to provide a method for treating a mammal affected with septic shock, cachexia, rheumatoid arthritis, inflammatory bowel disease or multiple sclerosis which comprises the administration of an agent which is an inhibitor of inflammatory cytokines.

It is thus a further object of the present invention to provide an AIDS therapy which, in addition to decreasing cachexia, decreases viral load, by administration of a hydroxyalkylammonium-pyrimidine or purine or nucleoside which inhibits inflammatory cytokines.

It is a still further object of the present invention to provide a therapeutic agent which inhibits the development of cachexia by inhibiting TNF and other inflammatory cytokines which are mediators of this disease.

Yet another aspect of the present invention provides a pharmaceutical formulation comprising a compound of Formula I, together with one or more pharmaceutically acceptable carriers, excipients or diluents.

DETAILED DESCRIPTION OF THE INVENTION

The compounds of Formula I are pyrimidine or purine and pyrimidine or purine nucleoside derivatives wherein the pyrimidine base portion is derived from thymine or the purine base portion is derived from a 2-substituted or a 2,6-substituted purine base. Where the compound of Formula I contains the substituted furanyl group of the formula

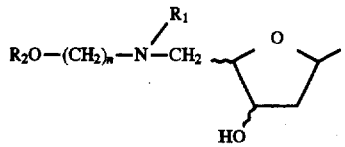

the compounds are nucleoside derivatives.

In Formula I, the group —(CH$_2$)—$_n$ wherein n is an integer from 2 to 6, represents an alkylene group of 2 to 6 carbon atoms. Representatives of such groups are ethylene, propylene, butylene, pentylene, hexylene, and their corresponding branched chained isomers.

The lower alkyl groups represented by R', R" and R$_1$ in Formula I contain 1 to 6 carbon atoms and are represented by methyl, ethyl, propyl, butyl, pentyl and hexyl. Similarly, the lower alkenyl and lower alkynyl groups contain 1 to 6 carbon atoms and one or more degrees of unsaturation.

The aralkyl groups include phenyl-, optionally substituted by one or more halogen or lower alkyl groups.

The R$_2$ alkanoyl groups of Formula I include both saturated and unsaturated alkanoyl containing from 2 to 20 carbon atoms, with the saturated alkanoyl groups containing 8 to 16 carbon atoms, i.e., octanoyl, nonanoyl, decanoyl, undecanoyl, dodecanoyl, tridecanoyl, tetradecanoyl, pentadecanoyl and hexadecanoyl, being preferred.

The halogen substituent may be a fluorine, chlorine, bromine or iodine substituent.

The compounds of Formula I contain asymmetric carbon atoms which give rise to various stereoisomers. The present invention includes the racemic mixtures, as well as the optically pure compounds of Formula I.

Equivalent to the compounds of Formula I for the purposes of this invention are the biocompatible and pharmaceutically acceptable salts thereof. Such salts can be derived from a variety of organic and inorganic acids including, but not limited to, methanesulfonic, hydrochloric, hydrobromic, hydroiodic, toluenesulfuric, sulfuric, maleic, acetic and phosphoric acids. When the nitrogen atom is quaternized, the compounds of Formula I exist in such salt form.

The novel pyrimidine or purine compounds of Formula I wherein R is a group of the formula

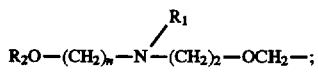

wherein n, R$_1$, and R$_2$ are as hereinbefore defined, are prepared as shown in Scheme I below:

Scheme I

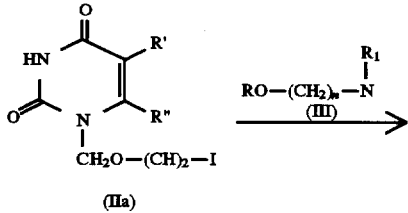

(IIa)

-continued
Scheme I

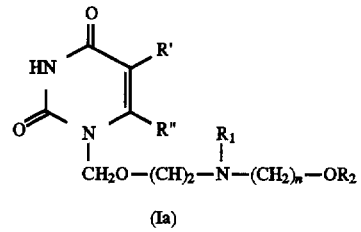

(Ia)

wherein n, R$_1$, R$_2$, R' and R" are as hereinbefore defined. (Pyrimidine base exemplified, purine base reaction is identical with the iodoethoxymethyl substituent being attached at N$^9$).

In reaction Scheme I, a 1-[(2-iodoethoxy)methyl] pyrimidine of formula II wherein R', R and R" are as hereinbefore defined, or a 9-[(2-iodoethoxy)methyl]purine wherein R' and R'" are as hereinbefore defined, is reacted with the appropriately substituted amine of Formula III wherein n, R and R$_1$ are as hereinbefore defined, to afford the desired pyrimidine of Formula Ia, or the appropriately substituted purine.

The amine of Formula III can be either a secondary amine or a tertiary amine depending upon whether the desired compound of Formula Ia contains one or two R$_1$ groups.

This reaction is typically conducted in an anhydrous polar solvent, such as acetonitrile. Typical reaction times are 2 to 6 hours, and usually the reaction is conducted at reflux temperature.

In Scheme II, a synthetic process for the nucleoside compounds of Formula I wherein R is a group of the formula

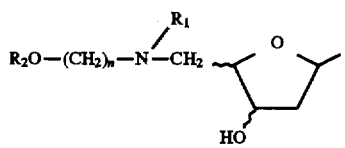

wherein n, R$_1$, R$_2$, and the wavy lines are as hereinbefore defined, is shown:

Scheme II

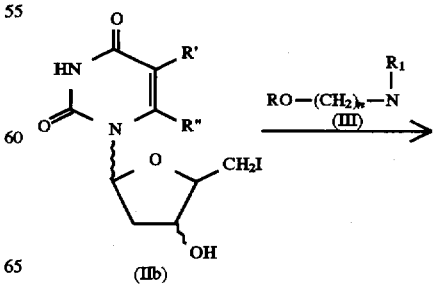

(IIb)

-continued
Scheme II

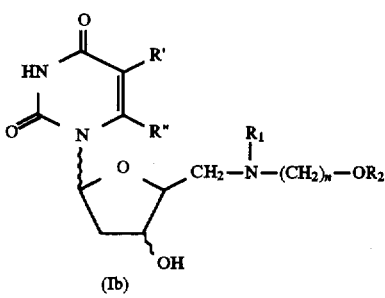

(Ib)

wherein R', R", n, $R_1$ and $R_2$ are as hereinbefore defined. (Pyrimidine base exemplified, purine base reaction identical with the 5-iodomethylfuranyl group substituent being attached at the $N^9$).

In reaction Scheme II, a 5-iodomethylfuranylnucleoside of Formula IIb wherein R' and the wavy lines are as hereinbefore defined, is reacted with the appropriately substituted amine of Formula III wherein n, $R_1$ and $R_2$ are as hereinbefore defined to afford the desired pyrimidine of Formula Ib, or the appropriately substituted purine.

As in Scheme I, the amine of Formula III utilized in Scheme II can be either a secondary amine or a tertiary amine depending upon whether the desired compound of Formula Ib contains one or two $R_1$ groups.

This reaction is typically conducted in an anhydrous polar solvent, such as acetonitrile. Typically, the reaction is conducted at reflux temperatures, with typical reaction times being from 4 to 24 hours.

The utility of the compounds of Formula I as inhibitors of inflammatory cytokines can be demonstrated by activity in standardized assays, described below.

Unless otherwise described the medium for human cell culture assays is defined as follows: RPMI-1640 is supplemented with 100 U/ml penicillin, 100 µg/ml streptomycin, 2 mM L-glutamine; 1 mM Na pyruvate; 1% MEM nonessential amino acids and 25 mM HEPES; (all from GIBCO, Gaithersburg, Md.). Complete medium is defined as medium supplemented with 5% pooled, heat-inactivated (56° C., 30 min.) human AB serum (Pel-freeze, Brown Deer, Wis.).

Inhibition of LPS-stimulated Cytokine Production in Whole Blood:

Citrated venous blood was obtained from phlebotomized normal donors and aliquoted into 1 ml volumes in 1.5 ml Eppendorf microcentrifuge tubes (Brinkman Instruments, Westbury, N.Y.). Test compound was prepared by making a 100 mM stock solution in 100% DMSO with all subsequent 1/10 dilutions also made in 100% DMSO. Test compound (1.0 µl) or DMSO alone was then added to 1 ml whole blood so that the final DMSO content was 0.1%. The samples were then rotated at 37° C. for 1 hour whereupon LPS (S. typhosa, SIGMA, St. Louis, Mo.) was added to the appropriate samples to a final concentration of 10 ng/ml. All samples were rotated at 37° C. for an additional 14 hours whereupon plasma was harvested by spinning at high speed in a microcentrifuge for 2-3 minutes. Samples were then diluted to 1/25, 1/100 and 1/250 in PBS and assayed by ELISA (R & D Systems, Minneapolis, Minn.) for TNF-α, IL-1β and In-6, respectively.

Endotoxin Testing:

All batches of media and reagents are tested to ensure they are free of endotoxins before they are used. This laboratory uses a kinetic chromogenic procedure (Kinetic QCL; Whittaker Bioproducts) for the determination of endotoxin, performed using the Thermomax Plate reader from Molecular Devices. The plate reader incorporates dedicated software for the computer analysis of all data. Samples are tested following the manufacturer's instructions, at 3 different concentrations, in triplicate. Reference Standard Endotoxin (United States Pharmacopeia) obtained at a concentration of 10,000 endotoxin units/ml, is used to generate a standard curve to determine the actual concentration of endotoxin in the samples (sensitivity =/>0.005 endotoxin units/ml).

Human Peripheral Blood Mononuclear Cell (PBMC) Isolation:

Venous blood is obtained from healthy volunteers and mixed with an equal volume of sterile isotonic saline/10 mM HEPES and placed into 50 ml conical polypropylene tubes in 30 ml aliquots. Each aliquot of diluted blood is underlaid with 20–25 ml of sterile Lymphocyte Separation Medium (LSM; Organon-Technika, Durham, N.C.). The tubes are centrifuged at 400 g for 40 minutes at room temperature. The mononuclear cells at the interface are removed and washed twice in sterile isotonic saline/10 mM HEPES followed by a wash in Hank's Balanced Salt Solution (HBSS) or RPMI without serum, depending on their intended use. Cell concentrations for each donor are determined by counting in a haematology and analyser (Serono-Baker).

PBMC Proliferation to Mitogens (PHA):

PBMC are adjusted to $4\times10^6$/ml in complete medium. To each well of a 96 well flat bottom tissue culture plate (Falcon 3072) is added 50 µl of cell suspension. Test materials (diluted in complete medium to 2× the desired final concentration) are added in 100 µl volumes to each well. All samples are tested in quadruplicate at four concentrations (spanning 3 $logs_{10}$). Control wells receive complete medium alone. Background response wells receive an additional 50 µl of complete medium, while all other wells receive 50 µl mitogen (diluted in complete medium to 4× the desired final concentration). Dexamethasone (50 µl) at a final concentration of 10 nM is included in each assay as an internal standard for inhibition. The mitogens used and their final concentrations are: OKT3 (anti-CD3 antibody; 100 ng/ml; Ortho) and PHA (phytohaemagglutinin A; 1.0 µg/ml; Sigma). The plates are then incubated for 3 days at 37° C. in humidified 5% $CO_2$, pulsed for the final 6 hours with 0.5 µCi/well of $^3$H-thymidine (6.7 Ci/mmole; Amersham, Arlington Heights, Ill.) in 50 µl complete medium. The contents of the wells are harvested onto glass fibre filters using a multiple automated sample harvester (Tomtec), and the incorporated $^1$H-thymidine determined by liquid scintillation spectrophotometry and represented an cpm (counts per minute) incorporated per well.

Two-Way Mixed Lymphocyte Reaction (MLR):

PBMC are prepared as described for the mitogen assays, but resuspended to $2\times10^6$ cells/ml in complete medium. Fifty µl of cell suspension from two different individuals is then added to each well of a 96-well flat bottom tissue culture plate. An additional 100 µl of complete medium, dexamethasone or test compounds are then added to each well, the plates are incubated for 6 days at 37° C., and then pulsed with $^3$H-thymidine and harvested as previously described.

Monocyte Release of Cytokines and Growth Factors:

Monocytes are prepared by centrifugal counterflow elutriation from peripheral blood mononuclear cells obtained from leukophoresis of normal volunteers (leukopaks) at Duke University, Durham, N.C. A panel has been compiled of 24 healthy donors who have been pre-screened and whose peripheral blood mononuclear cells (PBMC) have been found to respond in a normal manner to mitogenic stimulation and stimulation by a specific antigen (tetanus toxoid).

Their monocytes have also been found to respond in a normal manner when activated with lipopolysaccharide (LPS) in vitro.

Total cells are taken from leukopaks before elutriation and used to carry out in vitro assays measuring human PBMC responses to mitogens and antigens, PBMC obtained by separation on a LSM gradient (as described above) are resuspended in PBS and separated, using a Beckman elutriator, into lymphocytes and monocytes. Yields of $10^9$ monocytes with greater than 90% purity are routinely obtained.

Purified monocytes prepared as described above are suspended at $4 \times 10^6$ cells/ml in complete medium. To each well of a 48-well flat bottomed tissue culture plate is added 0.125 ml of cell suspension. Test materials (diluted in complete medium at 2× the desired final concentration) are added in 250 μl volumes to each well. Control wells receive 250 μl of complete medium or 250 μl of IL-4 (diluted to ×2 the desired final concentration of 50 ng/ml). All samples are tested at four concentrations in the presence or absence of 100 ng/ml LPS (125 μl of 4× desired final concentration added) and incubated at 37° C. in humidified 5% CO2, for 16 hours. At this time, culture supernatants are aspirated off, and the unattached cells and cell debris are removed by a 2 minute spin in a microcentrifuge at 10,000 g. The release of cytokines and growth factors is determined in the cell-free supernatants using ELISA capture assays. In this way, testing for IL-1β, TNF-α, IL-1 receptor antagonist, IL-6, IL-8, GM-CSF and PDGF is conducted.

Monocyte Procoagulant Activity (Tissue Factor):

The adhered monocytes remaining on the 48-well tissue culture plates after removal of the supernatants above, are used to measure levels of Tissue Factor production. The cells are solubilized overnight at 4° C. in 10% Triton-X100 in PBS, diluted to 1% Triton-X100 with PBS then assayed by ELISA for Tissue Factor.

Monocyte Release of $PGE_2$, $LTB_4$, and PAF:

Monocytes isolated as described above, were washed and resuspended in RPM1 containing 5 mg/ml HSA at $2 \times 10^6$ cells/ml and added to wells of a 48-well plates. The cells were allowed to adhere for 2 hours then washed in HBSS-BSA-HEPES buffer. Test materials were added at four concentrations (175 μl) for 60 minutes; then the monocytes were stimulated by addition of 300 mg/ml zymosan A (175 μl of 2× desired final concentration added). Supernatant medium was collected from the wells after 90 minutes incubation and stored at −20° C. until assayed. Supernatants were assayed for $PGE_2$, $LTB_4$ or PAF using specific scintillation proximity assays (SPA).

Monocyte Superoxide Anion ($O_2$) Release:

Monocytes are prepared as described above and resuspended to $5 \times 10^6$/ml in HBSS containing 10 Mm HEPES, 2 g/l glucose, 0.1% BSA, Ph 7.2. To each well of a 96-well flat bottom, tissue culture plate is added 100 μl of cell suspension and 100 μl of buffer or test materials. Samples are run in quadruplicate. The plate is incubated for 60 min. at 37° C. followed by the addition of 50 μl of buffer containing cytochrome C (5 mg/ml; type VI, horse heart, Sigma) and bovine liver catalase (1500 U/ml; Sigma) in the presence of zymosan A (PMA; 750 μg/ml; Sigma). The plate is incubated an additional 120 minutes at 37° C. during which the absorbance at 550 nm is monitored using a microplate reader incorporating dedicated software for kinetic analysis (Molecular Devices; Menlo Park, Calif.).

Inhibition of Monocyte Chemotaxis:

Monocytes are prepared as previously described, and resuspended at $5 \times 10^6$ cells/ml in HBSS, 0.1% BSA (HBSS-BSA). Fluorophore labeling of the cells is carried out by adding calcein-AM to the above cells at a final concentration of 2 μM. Following a 30 minute incubation at 37° C. in humidified 5% $CO_2$, the labeled monocytes are washed twice and incubated in a range of dilutions of the test materials for 60 minutes at 37° C. in humidified 5% $CO_2$. The pre-treated, calcein-AM loaded cells are then added in triplicate to the wells of the top compartment of a Neuro-Probe (Cabin, John, M.D.) 96-well chemotaxis chamber ($2 \times 10^5$ cells/well) and permitted to migrate through a 10 μm thick bonded polycarbonate membrane (5 μm porosity; NeuroProbe Inc; Cabin, John, M.D.) towards the wells of the lower compartment containing the chemoattractant (FMLP) at $5 \times 10^{-9}$ M. After a 90 minute incubation at 37° C. in a humidified chamber, the wells of the upper chambers are aspirated, the monocyte-associated membrane removed, non-migrating cells wiped off and the filters permitted to air dry to 15 minutes. The number of cells migrating through the membranes are quantified by measuring the fluorescent intensity of the migrating cells in a fluorescent microplate reader (CytoFluor 2300, Millipore Corp., Bedford, Mass.)

Monocyte Adherence to Vascular Endothelial Cells:

Human umbilical vein endothelial cells (HUVEC) are obtained from Clonetics (San Diego; Calif.). Confluent layers of epithelial cells are prepared by seeding 96-well plates with $2 \times 10^4$ cells/well and incubating at 37° C. in humidified 5% $CO_2$ for 24 hours. TNFα (50 μg) was then added to each well (10 μl of a 5 ng/ml stock solution) prior to the addition of monocytes. Monocytes are fluorescently labelled and pre-treated with test materials as described above, resuspended in complete medium to a final concentration of $2 \times 10^6$ cells/ml and incubated in triplicate in wells (100 μl/well) for 60 minutes at 37° C. in humidified 5% $CO_2$. Plates are then sealed and centrifuged at 250 g for 5 minutes to remove non-adhered monocytes and the number of adhered cells determined by reading plates on a fluorescent microplate reader.

When tested in the above standardized assays, a representative compound of Formula I, i.e., N,N-dimethyl-N-2-(hexadecanoyloxy)ethyl-N-[$N^1$-5-methyl-2,4-dioxopyrimidinyl)methoxyethyl]ammonium iodide was found to give the results shown below in Table 1.

TABLE 1

| COMPOUND: N,N-dimethyl-N-2-hexadecanoyloxy)ethyl-N-[$N^1$-5-methyl-2,4-dioxopyrimidinyl)methoxyethyl]ammonium iodide | | |
|---|---|---|
| ASSAY | EFFECT | UNITS: μm $EC_{50}$ |
| ENDOTOXIN | NE | |
| PHA | NE | |
| MLR | NE | |
| GM-CSF | INHIB | 12.6 |
| IL1β | INHIB | 7.5 |
| ILra | NT | |
| IL6 | INHIB | 5.7 |

TABLE 1-continued

COMPOUND:
N,N-dimethyl-N-2-hexadecanoyloxy)ethyl-N-[N$^1$-5-methyl-2,4-dioxopyrimidinyl)methoxyethyl]ammonium iodide

| ASSAY | EFFECT | UNITS: μm EC$_{50}$ |
|---|---|---|
| IL8 | INHIB | 2.9 |
| TNFα | INHIB | 5.5 |
| TISSUE FACTOR | INHIB | 4.30 |
| PGE$_2$ | NE | |
| LTB$_4$ | NE | 100.00 |
| PAF | NE | |
| SUPEROXIDE | INHIB | 34 |
| CHEMOTAXIS | INHIB | 47 |
| MTS | TC | 100.00 |
| LDH | TC | 100.00 |

Key:
NE No effect
NT Not tested
INHIB Inhibition
STIM Stimulation
IC$_{20}$ 20% Inhibitory Concentration
EC$_{50}$ 50% Effective Concentration
TC Tolerated Concentration Additionally, the compounds of Formula I exhibit activity as antiherpes, anti-tumor and antiviral agents when tested in standardized assays for such activity.

The ability of the compounds of Formula I to inhibit the action of various inflammatory cytokines make them useful in a wide variety of therapeutic methods. Specifically, their ability to mediate or inhibit the actions of TNF-a makes these compounds useful in the treatment of various invasive diseases, infections, and inflammatory states. Particularly important is the inhibition of the large amount of TNF produced during serious bacterial infections, which can trigger a state of shock and tissue injury (septic shock syndrome).

A further important use of the compounds of Formula I is to inhibit the TNF which is known to mediate cachexia produced during chronic disease states. Thus, these compounds are particularly useful in adjunctive therapy for AIDS and cancer patients to reduce and/or ameliorate the consequences of cachexia produced during these chronic disease states.

A further specific method of treatment for which the compounds of the instant invention are particularly useful is in the treatment of rheumatoid arthritis wherein increased amounts of the inflammatory cytokines, TNF-a and IL-1 are present. By virtue of their ability to mediate and/or inhibit the action of these cytokines, inflammation and the severity of the disease state can be reduced or eliminated.

The compounds of the instant invention can also be utilized in the treatment of multiple sclerosis (MS), Crohn's disease and ulcerative colitis by inhibiting and the activity of the inflammatory cytokines which underlie these disease states.

The compounds of the present invention are likewise useful in the therapeutic methods described in U.S. Pat. No. 5,306,732 by virtue of their ability to act as antagonists of tumor necrosis factor.

The compounds for use in the methods of the present invention can be, and are preferably, administered as medicaments, i.e., pharmaceutical compositions.

The pharmaceutical compositions used in the methods of this invention for administration to animals and humans comprise the compounds of Formula I in combination with a pharmaceutical carrier or excipient.

The medicament can be in the form of tablets (including lozenges and granules), dragees, capsules, pills, ampoules or suppositories comprising the compound of the invention.

"Medicament" as used herein means physically discrete coherent portions suitable for medical administration. "Medicament in dosage unit form" as used herein means physically discrete coherent units suitable for medical administration, each containing a daily does or a multiple (up to four times) or a sub-multiple (down to a fortieth) of a daily dose of the active compound of the invention in association with a carrier and/or enclosed within an envelope. Whether the medicament contains a daily dose or, for example, a half, a third or a quarter of a daily dose will depend on whether the medicament is to be administered once or, for example, twice, three times a day, respectively.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction of a physician or veterinarian.

The compounds of Formula I can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (g) adsorptive carriers, e.g., kaolin and bentonite; (i) lubricants, e.g., talc, calcium and magnesium stearate and solid polyethylene glycols.

The tablets, dragees, capsules and pills comprising the active compound can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The compounds of Formula I can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil, glycerol, tetrahydrofurfuryl alcohol, polyethylene glycols and fatty acid esters of sorbitol or mixtures thereof.

For parental administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), microcrystalline cellulose, aluminum methahydroxide, bentonite, agar-agar and tragacanth, or mixtures thereof.

The pharmaceutical compositions can also contain coloring agents and preservatives, as well as perfumes and flavoring additions (e.g., peppermint oil and eucalyptus oil), and sweetening agents, (e.g., saccharin and aspartame).

The pharmaceutical compositions will generally contain from 0.5 to 90% of the active ingredient by weight of the total composition.

In addition to the compounds of Formula I, the pharmaceutical compositions and medicaments can also contain other pharmaceutically active compounds.

Any diluent in the medicaments of the present invention may be any of those mentioned above in relation to the pharmaceutical compositions. Such medicaments may include solvents of molecular weight less than 200 as the sole diluent.

It is envisaged that the compounds of Formula I will be administered perorally, parenterally (for example, intramuscularly, intraperitoneally, subcutaneously, transdermally or intravenously), rectally or locally, preferably orally or parenterally, especially perlingually, or intravenously.

The dosage rate, e.g., 0.05 to 20 mg/kg of body weight, will be a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

The present invention will be better understood from a consideration of the following examples, which describe the preparation of compounds and compositions illustrative of the present invention. It will be apparent to those skilled in the art that many modifications, both of materials and methods, may be practiced without departing from the purpose and intent of this disclosure.

EXAMPLES

All melting points were taken on a Thomas Hoover melting point apparatus and are uncorrected. Infrared spectra (IR) were recorded on a Perkin-Elmer 1320 spectrophotometer. $^1$H NMR spectra were obtained using a Bruker AC-300 NMR. The assignment of complex NMR signals was accomplished by comparison with known standard spectra. The chemical shifts were reported in parts per million relative to an internal standard of tetramethylsilane. Elemental analyses were performed by Atlantic Microlab Inc., Norcross, Ga. Due to the hygroscopic nature of some of the quaternary ammonium compounds, their structures were confirmed by high resolution mass spectroscopy by using a VG70-SQ spectrometer. Thin layer chromatography (TLC) was performed on 1×3 inch fluorescent precoated Whatman Silica Gel 60 Å TLC plates. The TLC plates were visualized by UV light, iodine vapor, or charring following sulfuric acid spray. Silica gel (70–230 mesh) from Fisher Scientific was used for column chromatography. Reagents were purchased from Aldrich. Solvents, including acetonitrile, N,N-dimethylformamide (DMF), methylene chloride, and tetrahydrofuran (THF), were dried by placement over molecular sieves (4 Å) for 2 weeks before use.

Example A

2-Acetoxyethyl acetoxymethyl ether:

A mixture of dioxolane (35 mL, 0.5 mol) and acetic anhydride (42.5 mL, 0.5 mol) was cooled in ice to 0° C. Concentrated H2SO4 (0.3 mL, 0.005 mol) was added dropwise with stirring. Gas evolution occurred immediately, and the temperature rose slightly. The reaction mixture was allowed to warm to room temperature and stirred overnight. The reaction mixture was then poured into saturated ice-cold NaHCO3 solution (200 mL) and extracted with CHCl3 (150 mL). The chloroform layer was washed with saturated NaHCO3 and dried over anhydrous Na2SO4. The drying agent was suction filtered, and evaporation of chloroform yielded a liquid, which was distilled under vacuum at 0.9 mmHg. After the removal of a small amount of low boiling material, the product was obtained at 46° C. at 0.9 mmHg (lit. bp 120°–130° C. at 30 mmHg). Yield 58%; Wt. 51.5 g; IR (neat) 2950 (aliphatic CH) and 1730 (CO ester) cm$^{-1}$; $^1$H NMR (CDCl3) 1.9–2.1 (s, CH3CO), 3.6–3.8 (t, COOCH2 CH2O), 4.0–4.2 (t, CO O CH2CH2O), 5.1–5.3 (s, OCH O). The product was used in the next example without further purification.

Example B

1-[(2-Acetoxyethoxy)methyl]thymine:

Thymine (0.63 g, 5 mmol) was added to 2-acetoxyethyl acetoxymethyl ether (1.32 g, 7.5 mmol) dissolved in 2 (15 mL). The reaction mixture was stirred at room temperature and N,O-bis(trimethylsilyl)acetamide (2.96 mL, 12 mmol) was added dropwise. After 3 hours of stirring, the clear solution was cooled to 0° C., and SnCl4 (0.12 mL, 1 mmol) was added. The reaction mixture was allowed to come to room temperature and stirred overnight. A mixture of saturated aqueous NaHCO3 (25 mL) and CHCl3 (50 mL) was prepared and cooled in ice. The reaction mixture was added slowly with vigorous stirring; a white foam formed immediately. After filtration, the aqueous layer was further extracted with ethyl acetate (3×25 mL) and CHCl3 (25 mL), and the combined organic layers were dried over anhydrous Na2SO4. After filtration of drying agent and removal of solvents in vacuo, an oily liquid was obtained. It was purified on a silica gel column using 2:1 CHCl3/CH3COCH3 as the eluent to give the desired product. Yield 36%; Wt. 4.0 g; mp 105°–107° C.; $^1$H NMR (DMSO-d6) 1.8 (s, CH3 C5 thymine), 2.0 (s, CH3 CO), 3.65 (m, CO O CH2 CH2), 4.1 (m, CO O CH2 CH2), 5.05 (s, O CH2 N) , 7.55 (s, H C6 thymine), 11.3 (s, HN thymine).

Example C

1-[(2-hydroxyethoxy)methyl]thymine:

To a solution of 1-[(2-acetoxyethoxy)methyl]thymine (4 g, 16 mmol) in CH3OH (100 mL) was added NaOCH3 in CH3OH (20 mL, 1N). After 2 hours of stirring at room temperature, 1N HCl was added to adjust the pH to 4.0. Methanol and water were removed under vacuum to obtain a solid. The solid was dissolved in CH3OH and crystallized by dropwise addition of CHCl3; it was used in the next reaction without further purification. Yield 76%; Wt. 2.5 g; mp 154°–156° C.; $^1$HNMR (DMSO-d6) 1.75 (s, CH3 C5 thymine), 3.55–3.75 (A2B2 pattern, O CH2 CH2 O), 5.10 (s, O CH2 N), 7.55 (s, H C6 thymine), 11.3 (s, HN thymine).

Example D

1-[(2-Iodoethoxy)methyl]thymine:

Methyltriphenoxyphosphonium iodide (10 g, 24 mmol) was added in five aliquots to a solution of 1-[(2-hydroxyethoxy)methyl]thymine (2.5 g, 12 mmol) in dry DMF (70 mL). The reaction mixture was stirred at room temperature for 20 minutes, then CH3OH (3 mL) was added to decompose the unreacted methyltriphenoxyphosphonium iodide. After 20 minutes, DMF was removed under high vacuum, and the residue was dissolved in CHCl3 (50 mL). The chloroform solution was washed with sodium thiosulfate (2×25 mL, 1N) and water (2×25 mL), then dried over anhydrous Na2SO4. After filtration of drying agent and removal of CHCl3 in vacuo, a slightly yellow oil was obtained. The desired product was obtained through crystallization from chloroform by slow addition of hexane. Yield 80%; Wt. 3.0 g; mp 112°–115° C.; $^1$H NMR (CDCl3) 1.9 (s, CH3 C5 thymine), 3.25 (m, I CH2 CH2), 3.85 (m, I CH2 CH2), 5.20 (s, O CH2 N), 7.25 (s, H C6 thymine).

Example E

5'-iodothymidine:

Thymidine (0.97 g, 4 mmol) and methyltriphenoxyphosphonium iodide (2.18 g, 4.8 mmol) were dissolved in dry DMF (10 mL). The reaction mixture was stirred at room temperature for 20 minutes. Then methanol (5 mL) was added to decompose excess methyltriphenoxyphosphonium iodide. After stirring another 20 minutes, DMF was removed under high vacuum, and chloroform (30 mL) was added to the residue and stirred. The insoluble solid was filtered. The filtrate (slightly yellow) was washed with sodium thiosulfate (25 mL, 1N) and water (25 mL) and dried over magnesium sulfate. After filtration of drying agent, evaporation of chloroform gave a solid, which was combined with the solid obtained above and dissolved in CH3OH. Silica gel chromatography using chloroform/methanol (9:1) yielded 1 g of pure product. Yield 72%; mp 172°–175° C.; $^1$H NMR (pyridine-d5) 1.95 (s, CH3 C5 thymine), 2.45–2.65 (m, H2 C2'), 3.55–3.75 (m, H2 C5'), 4.20–4.30 (m, H C4'), 4.65–4.75 (m, H C3'), 6.90–7.00 (m, H C1'), 7.65 (s, H C6 thymine).

Example F

2-Bromoethyl octanoate:

2-Bromoethanol (4 g, 32 mmol) was added dropwise to a solution of octanoyl chloride (7.8 g, 48 mmol) and pyridine (5 mL) in benzene (50 mL). The reaction mixture was stirred at room temperature for 24 hours. After evaporation of benzene and pyridine under high vacuum, the residue was redissolved in benzene (100 mL). The solution was washed with water (50 mL), sulfuric acid solution (3×25 mL, 0.5N), sodium bicarbonate solution (25 mL, 1N), and water (2×75 mL). The benzene layer was dried over Na2SO4. The drying agent was suction filtered, and the benzene was evaporated. The resulting oil was purified by silica gel chromatography using chloroform/methanol (9:1) to give 6.5 g of pure product. Yield 81%; liquid; IR (neat) 2930 and 2850 (aliphatic CH), 1730 (CO ester) cm$^{-1}$; $^1$H NMR (CDCl3) 0.85–0.95 (t, CH3 (CH2)4), 1.20–1.40 (m, CH3 (CH2)4), 1.55–1.70 (m, CH2 CH2 CO), 2.25–2.40 (t, CH2 CH2 CO), 3.50–3.60 (t, O CH2 CH2 Br), 4.35–4.40 (t, O CH2 CH2 Br).

Example G

2-Bromoethyl hexadecanoate:

This intermediate was prepared in a manner analogous to that of 2-bromoethyl octanoate from 2-bromoethanol (4 g, 32 mmol), hexadecanoyl chloride (13.2 g, 48 mmol), and pyridine (5 mL) in benzene (50 mL). Silica gel chromatography using chloroform/methanol (9:1) yielded 9.75 g pure product. Yield 84%; liquid; $^1$H NMR (CDCl3) 0.85–0.95 (t, CH3 (CH2)12), 1.20–1.40 (m, CH3 (CH2)12), 1.55–1.70 (m, CH2 CH2 CO), 2.25–2.40 (t, CH2 CH2 CO), 3.50–3.60 (t, O CH2 CH2 Br), 4.35–4.40 (t, O CH2 CH2 Br).

Example H

3-Bromopropyl hexadecanoate:

This intermediate was prepared in a manner analogous to that of 2-bromoethyl octanoate from 3-bromo-1-propanol (2.53 g, 18 mmol), hexadecanoyl chloride (6.25 g, 22.5 mmol), and pyridine (4 mL) in benzene (50 mL). Silica gel chromatography using chloroform/methanol ( 9:1) yielded 5.7 g pure product. Yield 69%; liquid; $^1$H NMR (CDCl3) 0.85–0.95 (t, CH3 (CH2)12), 1.20–1.40 (m, CH3 ( CH2)12), 1.55–1.70 (m, CH2 CH2 CO), 2.13–2.23 (m, O CH2 CH2 CH2 Br), 2.28–2.38 (t, CH2 CH2 CO), 3.45–3.50 (t, O CH2 CH2 CH2 Br), 4.35–4.40 (t, O CH2 CH2 CH2 Br).

Example I 2-(Dimethylamino)ethyl octanoate:

2-Bromoethyl octanoate (0.2 g, 0.72 mmol) and 40% aqueous dimethylamine (4.2 mL, 36 mmol) were dissolved in acetonitrile (10 mL). The reaction mixture was stirred at room temperature for 48 hours. After removal of acetonitrile under vacuum, chloroform (30 mL) was added. The chloroform layer was extracted with potassium carbonate solution (20 mL, 0.01N) and water (2×20 mL), then was dried over sodium sulfate. The drying agent was suction filtered, and the chloroform removed in vacuo. The resulting material was applied to a silica gel column (discontinuous gradient of chloroform/methanol 95:5, 8:2 as eluent) affording 0.13 g pure product. Yield 77%; liquid; $^1$H NMR (CDCl3) 0.85–0.95 (t, CH3 (CH2)4), 1.20– 1.40 (m, CH3 (CH2)4), 1.55–1.70 (m, CH2 CH2 CO), 2.25–2.40 (t, CH2 CH2 CO), 2.45–2.55 (s, (CH3)2 N) 2.75–2.85 (t, O CH2 CH2 N), 4.25–4.35 (t, O CH2 CH2 N).

Example J 2-(Dimethylamino)ethyl hexadecanoate:

This intermediate was prepared in a manner analogous to that of 2-(dimethylamino)ethyl octanoate from 2-bromoethyl hexadecanoate (0.2 g, 0.55 mmol) and 40% aqueous dimethylamine (3.5 mL, 27.5 mmol) in acetonitrile (10 mL). The resulting product was applied to a silica gel column (discontinuous gradient of chloroform/methanol 95:5, 8:2 as eluent) affording 0.13 g pure product. Yield 72%; mp 46°–48° C.; $^1$HNMR (CDCl3) 0.85–0.95 (t, CH3 (CH2)12), 1.20–1.40 (m, CH3 (CH2)12), 1.55–1.70 (m, CH2 CH2 CO), 2.25–2.40 (t, CH2 CH2 CO), 2.45–2.55 (s, (CH3)2 N) 2.75–2.85 (t, O CH2 CH2 N), 4.25–4.35 (t, O CH2 CH2 N).

Example K 3-(Dimethylamino)propyl hexadecanoate:

This intermediate was prepared in a manner analogous to that of 2-(dimethylamino)ethyl octanoate from 3-bromopropyl hexadecanoate (3 g, 7.95 mmol) and 40% aqueous dimethylamine (15 mL, 119 mmol) in acetonitrile (20 mL). The resulting material was applied to a silica gel column (discontinuous gradient of chloroform/methanol 95:5, 8:2 as eluent) affording 1.3 g pure product. Yield 72%; mp 49°–50° C.; $^1$H NMR (CDCl3) 0.85–0.95 (t, CH3 (CH2)12), 1.20–1.40 (m, CH3 (CH2)12), 1.55–1.70 (m, CH2 CH2 CO), 1.88–2.00 (m, O CH2 CH2 CH2 N), 2.27–2.35 (t, CH2 CH2 CO), 2.37–2.45 (s, (CH3)2 N) 2.50–2.62 (t, O CH2 CH2 CH2 N), 4.10–4.18 (t, O CH2 CH2 CH2 N).

Example 1

N,N-Dimethyl-N-2-hydroxyethyl-N-[N$^1$-(5-methyl-2,4-dioxopyrimidinyl)methoxyethyl]ammonium iodide:

1-[(2-Iodoethoxy)methyl]thymine (100 mg, 0.32 mmol) and 2-dimethylaminoethanol (34.5 mg, 0.38 mmol) were dissolved in acetonitrile (10 mL). The reaction mixture was heated to a gentle reflux and stirred for 5 hours. After cooling to room temperature, 77 mg of pure product was obtained through crystallization by slow addition of ethyl ether. Yield 59%; mp 158°–161° C.; $^1$H NMR (CD3CN) 1.85–1.88 (s, CH3 C5 thymine), 3.10–3.15 (s, (CH3)2 N), 3.30 (s, HO CH2), 3.45–3.48 (m, N CH2 CH2 O), 3.55–3.58 (m, HO CH2 CH2 N), 3.90–4.00 (m, HO CH2 CH2 N CH2 CH2 O), 5.10 (s, O CH2 N), 7.30 (s, H C6 thymine). Elemental Analysis (C12H22N3O4I); Calcd. C, 36.10%; H, 5.56%; N, 10.53%; Found C, 36.17%; H, 5.57%; N, 10.43%

Example 2

N,N-Dimethyl-N-3-hydroxypropyl-N-[N$^1$-(5-methyl-2,4-dioxopyrimidinyl)methoxyethyl]ammonium iodide:

The title compound was synthesized in a manner analogous to that of the compound of Example 1 from 1-[(2-iodoethoxy)methyl]thymine (100 mg, 0.32 mmol) and 3-dimethylamino-1-propanol (40 mg, 0.38 mmol) in acetonitrile (10 mL). Yield 59%; mp 178°–180° C.; $^1$H NMR (DMSO-d6) 1.75–1.80 (s, CH3 C5 thymine), 1.75–1.90 (m, HO CH2 CH2 CH2 N), 3.05–3.15 (s, (CH3)2 N), 3.40–3.50 (m, HO CH2 CH2 CH2 N), 3.50–3.60 (m, N CH2 CH2 O), 3.85–3.95 (m, HO CH2 CH2 CH2 N CH2 CH2 O), 4.75–4.85 (t, HO CH2), 5.05–5.10 (s, O CH2 N), 7.55–7.60 (s, H C6 thymine), 11.35–11.40 (s, HN thymine). Elemental Analysis (C13H24N3O4I); Calcd. C, 37.78%; H, 5.85%; N, 10.17%; Found C, 37.73%; H, 5.83%; N, 10.09%.

Example 3

N,N-Dimethyl-N-2,3-dihydroxypropyl-N-[N$^1$-(5-methyl-2,4-dioxopyrimidinyl)methoxyethyl]ammonium iodide:

The title compound was synthesized in a manner similar to that of the compound of Example 1 from 1-[(2-iodoethoxy)methyl]thymine (100 mg, 0.32 mmol) and 3-dimethylamino-1,2-propandiol (46 mg, 0.38 mmol) in acetonitrile (10 mL). Yield 55%; mp 163°–165° C.; $^1$H NMR (DMSO-d6) 1.75–1.80 (s, CH3 C5 thymine), 3.10–3.15 (s, (CH3)2 N), 3.60–3.70 (m, CH2 N CH2), 3.80–4.10 (m, HO CH2 CH(OH) CH2 N CH2 CH2 O), 4.95–5.00 (t, HO CH2), 5.05–5.10 (s, O CH2 N), 5.20–5.25 (d, HO CH2 CH(O H) CH2), 7.55–7.60 (s, H C6 thymine), 11.35–11.40 (s, HN thymine). Elemental Analysis (C13H24N3O5I); Calcd. C, 36.37%; H, 5.64%; N, 9.79%; Found C, 36.46%; H, 5.67%; N, 9.78%

Example 4

N-Methyl-N-2-hydroxyethyl-N-[N$^1$-(5-methyl-2,4-dioxopyridinyl)methoxyethyl]amine:

1-[(2-Iodoethoxy)methyl]thymine (200 mg, 0.65 mmol) and 2-(methylamino)ethanol (242 mg, 3.3 mmol) were dissolved in acetonitrile (8 mL). The reaction mixture was heated to a gentle reflux and stirred for 5 hours. After evaporation of acetonitrile, chloroform (50 mL) was added, and the solution was washed with sodium hydroxide solution (20 mL, 1N) and water (2×20 mL). The chloroform layer was then dried over anhydrous sodium sulfate. The drying agent was suction filtered, and the chloroform removed under vacuum. The resulting residue was purified by column chromatography using a discontinuous chloroform/methanol (9:1, 7:3) gradient to give 95 mg of pure product. Yield 60%; mp 58°14 60° C.; $^1$HNMR (CD3OD) 1.85–1.92 (s, CH3 C5 thymine), 2.25–2.35 (s, CH3 N), 2.55–2.60 (t, HO CH2 CH2 N CH2), 2.60–2.65 (t, HO CH2 CH2 N CH2), 3.55–3.70 (m, HO CH2 CH2 N CH2 CH2 O), 5.10–5.15 (s, O CH2 N), 7.45–7.50 (s, H C6 thymine). Elemental Analysis (C11H19N3O4); Calcd. C, 51.35%; H, 7.44%; N, 16.33%; Found C, 51.09%; H, 7.48%; N, 16.12%.

Example 5

N,N-Dimethyl-N-2-(octanoyloxy)ethyl-N-[N$^1$-(5-methyl-2,4-dioxopyrimidinyl)methoxyethyl]ammonium iodide:

1-[(2-Iodoethoxy)methyl]thymine (30 mg, 0.097 mmol) and 2-(dimethylamino)ethyl octanoate (100 mg, 3.9 mmol) were dissolved in acetonitrile (10 mL). The reaction mixture was heated to a gentle reflux and stirred for 24 hours. After the removal of acetonitrile under vacuum, benzene (5×20 mL) was added to the residue, and the solution was decanted to remove the unreacted starting material. Pure product (40 mg) was obtained by column chromatography (discontinuous gradient of CHCl3:MeOH 9:1, 7:3). Yield 74%; mp 96°–98° C.; hygroscopic; $^1$HNMR (CDCl3) 0.80–1.00 (t, CH3 (CH2)4), 1.20–1.40 (m, CH3 (CH2)4), 1.50–1.70 (m, CH2 CH2 CO), 1.85–1.95 (s, CH3 C5 thymine), 2.30–2.45 (m, CH2 CH2 CO), 3.30–3.60 (s, ( CH3)2 N), 3.90–4.10 (m, CH2 N CH2), 4.15–4.30 (m, CH2 CH2 O CH2 N1), 4.50–4.65 (m, C(O)O CH2), 5.20–5.35 (s, O CH2 N1). FAB Mass Spectrum (M)$^+$; Calcd. 398.2654 (C20H36O5N3); Found 398.2644 (2.5 ppm).

Example 6

N,N-Dimethyl-N-2-(hexadecanoyloxy)ethyl-N-[N$^1$-(5-methyl-2,4-dioxopyrimidinyl)methoxyethyl]ammonium iodide:

The title compound was synthesized in a manner analogous to the compound of Example 5 from 1-[(2-iodoethoxy)methyl]thymine (200 mg, 0.65 mmol) and 2-(dimethylamino)ethyl hexadecanoate (600 mg, 2.0 mmol) in acetonitrile (10 mL). Yield 49%; Wt. 203 mg; mp 144°–146° C.; $^1$H NMR (CDCl3) 0.80–1.00 (t, CH3 (CH2)12), 1.20–1.40 (m, CH3 (CH2)12), 1.50–1.70 (m, CH2 CH2 CO), 1.85–1.95 (s, CH3 C5 thymine), 2.30–2.45 (m, CH2 CH2 CO), 3.30–3.60 (s, (CH3)2 N), 3.90–4.10 (m, CH2 N CH2), 4.15–4.30 (m, CH2 CH2 O CH2 N1), 4.50–4.65 (m, C(O)O CH2), 5.20–5.35 (s, O CH2 N1), 7.35–7.40 (s, H C6 thymine), 9.95–10.25 (s, HN thymine). Elemental Analysis (C28H52O5N3I); Calcd. C, 52.74%; H, 8.22%; N, 6.59% Found C, 52.48%; H, 8.23%; N, 6.45%.

Example 7

N,N-Dimethyl-N-3-(hexadecanoyloxy)propyl-N-[N$^1$-(5-methyl-2,4-dioxopyrimidinyl)methoxyethyl]ammonium iodide:

The title compound was synthesized in a manner analogous to the compound of Example 5 from 1-[(2-iodoethoxy)methyl]thymine (200 mg, 0.65 mmol) and 3-(dimethylamino)propyl hexadecanoate (600 mg, 1.7 mmol) in acetonitrile (10 mL). Yield 29%; Wt. 120 mg; mp 133°–135° C.; $^1$H NMR (CDCl3) 0.80–1.00 (t, CH3 (CH2)12), 1.20–1.40 (m, CH3 (CH2)12), 1.50–1.70 (m, CH2 CH2 CO), 1.85–1.95 (s, CH3 C5 thymine), 2.15–2.28 (m, O CH2 CH2 CH2 N), 2.30–2.40 (m, CH2 CH2 CO), 3.30–3.50 (s, (CH3)2 N), 3.65–3.72 (m, CH2 N CH2 CH2 O), 3.90–4.03 (m, CH2 N CH2 CH2 O), 4.15–4.35 (m, CH2 CH2 O CH2 N1; C(O)O CH2), 5.20–5.35 (s, O CH2 N1), 7.35–7.40 (s, H C6 thymine), 9.80–9.85 (s, HN thymine). FAB Mass Spectrum (M)$^+$; Calcd. 524.4064 (C29H54O5N3); Found 524.4043 (3.9 ppm).

Example 8

N,N-Dimethyl-N-2-hydroxyethyl-N-[5'-(2,,5,dideoxythymidinyl)]ammonium iodide:

A solution of 5'-iodothymidine (0.5 g, 1.4 mmol) and 2-dimethylaminoethanol (5 mL, 49 mmol) in DMF (30 mL) was heated to 50° C. for 3 hours. After DMF was removed under high vacuum, chloroform (2×20 mL) was added to dissolve the unreacted starting material. After decanting the chloroform, the residue was purified via column chromatography ( chloroform/methanol discontinuous gradient 6:4 to 3:7) Yield 52%; Wt. 0.32 g; hygroscopic; $^1$H NMR (CD3OD) 1.90–2.00 (s, CH3 C5 thymine), 2.20–2.35 (m, H C2'), 2.42–2.55 (m, H C2'), 2.85–2.90 (d, HO C3'), 3.20–3.35 (s, N (CH3)2), 3.55–3.65 (t, HO CH2 CH2 N CH2), 3.85–3.95 (d, HO CH2 CH2 N CH2), 4.00–4.05 (m, HO CH2), 4.22–4.31 (H C4'), 4.35–4.42 (H C3'), 6.18–6.26 (t, H C1'), 7.50–7.55 (s, H C6 thymine). FAB Mass Spectrum (MH)$^+$; Calcd. 314.1716 (C14H24O5N3); Found 314.1731 (4.7 ppm).

Example 9

N-Methyl -N-hydroxyethyl-N-[5'-(2',5'-dideoxy)thymidinyl]amine:

The title compound was synthesized in a manner similar to that of the compound of Example 8 from 5'-iodothymidine (0.2 g, 0.57 mmol) and 2-(methylamino)ethanol (0.21 g, 2.8 mmol, 5 fold excess) in acetonitrile (8 mL). Yield 55%; Wt. 94 mg; hygroscopic; $^1$H NMR (CD3OD) 1.88–1.95 (s, CH3 C5 thymine), 2.20–2.35 (m, H C2'), 2.48–2.60 (m, H C2'), 2.68–2.70 (d, HO C3'), 2.81–2.90 (s, N CH3), 3.40–3.54 (m, HO CH2 CH2 N CH2), 3.75–3.80 (m, HO CH2 CH2 N CH2), 3.82–3.91 (m, HO CH2), 4.22–4.31 (H C4'), 4.35–4.42 (H C3'), 6.18–6.26 (t, H C1'), 7.50–7.55 (s, H C6 thymine). FAB Mass Spectrum (MH)$^+$; Calcd. 300.1559 (C13H22OSN3); Found 300.1562 (1.0 ppm).

Example 10

N,N-Dimethyl-N-3-hydroxypropyl-N-[5,-(2',5'-dideoxythymidinyl)]ammonium iodide:

The title compound was prepared in a manner analogous to that of the compound of Example 8 from 5'-iodothymidine (0.5 g, 1.4 mmol) and 3-dimethylamino-l-propanol (5.8 mL, 49 mmol) in DMF (30 mL). The compound was purified via column chromatography (discontinuous gradient of chloroform/methanol 6:4, 3:7). Yield 54%; Wt. 0.35 g; hygroscopic; $^1$H NMR (CD3OD) 1.90–1.95 (s, CH3 C5 thymine), 1.95–2.10 (HO CH2 CH2 CH2), 2.20–2.35 (m, H C2'), 2.42–2.55 (m, H C2'), 2.85–2.90 (d, HO C3'), 3.00–3.03 (t, HO CH2), 3.20–3.35 (s, N (CH3)2), 3.52–3.62 (m, HO CH2 CH2 CH2 N CH2), 3.85–3.95 (m, HO CH2 CH2 CH2 N CH2), 4.00–4.05 (m, HO CH2), 4.22–4.31 (H C4'), 4.35–4.42 (H C3'), 6.18–6.26 (t, H C1'), 7.50–7.55 (s, H C6 thymine). FAB Mass Spectrum (MH)$^+$; Calcd. 328.1872 (C15H26O5N3); Found 328.1882 (3.1 ppm).

Example 11

N,N-Dimethyl-N-[2-(octanoyloxy)ethyl]-N-[5'-(2',5'-dideoxy)thymidinyl]ammonium iodide:

The title compound was prepared according to the procedure described for the compound of Example 5 from 5'-iodothymidine (0.2 g, 0.57 mmol) and 2-(dimethylamino) ethyl octanoate (1 g, 4.0 mmol) in acetonitrile (10 mL). Yield 36%; Wt. 0.12 g; mp 103°–106° C.; hygroscopic; $^1$H NMR (CDCl3) 0.70–0.78 (t, CH3 (CH2)4), 1.11–1.23 (m, CH3 (CH2)4), 1.42–1.53 (m, CH2 CH2 CO), 1.70–1.75 (s, CH3 C5 thymine), 2.11–2.23 (m, H C2'), 2.18–2.25 (t, CH2 CH2 CO), 2.32–2.45 (m, H C2'), 3.12–3.18 (s, (CH3)2 N), 3.22 (s, HO), 3.65–3.72 (m, O CH2 CH2 N CH2), 3.75–3.82 (m, H C4'), 3.95–4.12 (m, O CH2 CH2 N CH2), 4.29–4.42 (m, H C3'; C(O)O CH2), 6.02–6.10 (t, H C1'), 7.40–7.43 (s, H C6 thymine). FAB Mass Spectrum (M)$^+$; Calcd. 440.2761 (C22H38O6N3); Found 440.2759 (0.45 ppm).

Example 12

N,N-Dimethyl-N-[2-(hexadecanoyloxy)ethyl]-N-[5'-(2',5'-dideoxy)-thymidinyl]ammonium iodide:

The title compound was prepared in a manner similar to that of the compound of Example 5 from 5'-iodothymidine (0.2 g, 0.57 mmol) and 2-(dimethylamino)ethyl hexadecanoate (0.6 g, 1.7 mmol) in acetonitrile (10 mL). Yield 30%; Wt. 0.12 g; mp 148°–150° C.; hygroscopic; $^1$H NMR (CDCl3) 0.70–0.78 (t, CH3 (CH2)12), 1.11–1.23 (m, CH3 ( CH2)12), 1.42–1.53 (m, CH2 CH2 CO), 1.70–1.75 (s, CH3 C5 thymine), 2.11–2.23 (m, H C2'), 2.18–2.25 (t, CH2 CH2 CO), 2.32–2.45 (m, H C2'), 3.12–3.18 (s, (CH3)2 N), 3.22 (s, HO), 3.65–3.72 (m, O CH2 CH2 N CH2), 3.75–3.82 (m, H C4'), 3.95–4.12 (m, O CH2 CH2 N CH2), 4.29–4.42 (m, H C3'; C(O)O CH2), 6.02–6.10 (t, H C1'), 7.40–7.43 (s, H C6 thymine). Elemental Analysis (C30H54O6N3I); Calcd. C, 53.01%; H, 8.01%; N, 6.18%; Found C, 53.06%; H, 8.02%; N, 6.09%.

Example 13

N,N-Dimethyl-N-[3-(hexadecanoyloxy)propyl]-N-[5'-(2',5'-dideoxy)thymidinyl]ammonium iodide:

The title compound was prepared in a manner similar to that of the compound of Example 5 from 5'-iodothymidine (0.2 g, 0.57 mmol) and 3-(dimethylamino)propyl hexadecanoate (0.6 g, 1.7 mmol) in acetonitrile (10 mL). Yield 36%; Wt. 0.14 g; very hygroscopic; $^1$H NMR (CDCl3) 0.70–0.78 (t, CH3 (CH2)12), 1.11–1.23 (m, CH3 ( CH2)12), 1.42–1.53 (m, CH2 CH2 CO), 1.70–1.75 (s, CH3 C5 thymine), 2.18–2.35 (t, CH2 CH2 CO), 2.28–2.68 (m, H2 C2'; O CH2 CH2 CH2 N), 3.22–3.42 (s, (CH3)2 N), 3.58–3.72 (m, O CH2 CH2 N CH2; H C4'), 4.12–4.30 (m, O CH2 CH2 N CH2), 4.48–4.56 (m, H C3'; C(O)O CH2), 6.02–6.10 (t, H C1'), 7.50–7.53 (s, H C6 thymine), 10.20–10.25 (s, HN thymine). FAB Mass Spectrum (M)$^+$; Calcd. 566.4169 (C31H56O6N3); Found 566.4178 (1.60 ppm).

Example 14

N,N-Dimethyl-N-3-hydroxypropyl-N-[N$^9$-(guanyl)methoxyethyl]ammonium iodide:

The title compound was synthesized in a manner analogous to that of the compound of Example 1 from 9-[(2-iodoethoxy)methyl]guanine (100 mg, 0.32 mmol) and 3-dimethylamino-1-propanol (40 mg, 0.38 mmol) in acetonitrile (10 mL).

Example 15

| Tablet Formulation | |
|---|---|
| Ingredient | mg/tablet |
| Compound of formula I | 50 |
| Starch | 50 |
| Mannitol | 75 |
| Magnesium stearate | 2 |
| Stearic acid | 5 |

The compound of formula I, a portion of the starch and the lactose are combined and wet granulated with starch paste. The wet granulation is placed on trays and allowed to dry overnight at a temperature of 45 degrees Centigrade. The dried granulation is comminuted in a comminutor to a particle size of approximately 20 mesh. Magnesium stearate, stearic acid and the balance of the starch are added and the entire mix blended prior to compression on a suitable tablet press. The tablets are compressed at a weight of 232 mg. using a 11/32" punch with a hardness of 4 kg.

What is claimed is:

1. A method for inhibiting inflammatory cytokines which comprises administration to a mammal in need of such therapy of a cytokine inhibitory amount of a compound of the Formula I

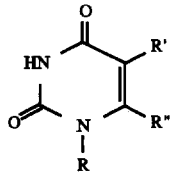

R is a group of the formula

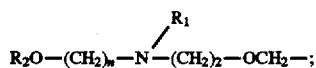

wherein $R_1$ is one or two lower alkyl groups with the proviso that when two lower alkyl groups are present, then the nitrogen atom is quaternized; $R_2$ is hydrogen or an alkanoyl group of 2–20 carbon atoms; n is 2–6; or R is a substituted furanyl group of the formula

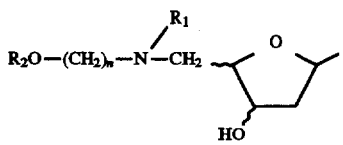

wherein $R_1$ and $R_2$ are as hereinbefore defined; and the wavy lines indicate either stereochemical configuration; R' and R" are independently hydrogen, halogen or a lower alkyl, lower alkenyl, lower alkynyl, or aralkyl group; R'" is hydrogen, halogen, alkylthio, amino, acylamino carbamyl or azide; and the pharmaceutically acceptable salts thereof.

2. A method according to claim 1 wherein R is a group of the formula

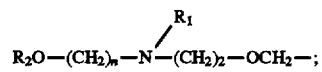

wherein n is 2–6;

$R_1$ is one or two lower alkyl groups with the proviso that when two lower alkyl groups are present, then the nitrogen atom is quaternized;

$R_2$ is hydrogen or an alkanoyl group of 2–20 carbon atoms; and their pharmaceutically acceptable salts.

3. The method according to claim 1 which is N,N-dimethyl-N-2-(hexadecanoyloxy)ethyl-N-[$N^1$-(5-methyl-2,4-dioxopyrimidinyl)methoxyethyl]ammonium iodide, or another pharmaceutically acceptable salt thereof.

4. The method according to claim 2 which is N,N-dimethyl-N-2-(octanoyloxy)ethyl-N-[$N^1$-(5-methyl-2,4-dioxopyrimidinyl)methoxyethyl]ammonium iodide, or another pharmaceutically acceptable salt thereof.

5. The method according to claim 2 which is N-methyl-N-(2-hydroxyethyl)-N-[$N^1$-(5-methyl-2,4-dioxopyrimidinyl)methoxyethyl]amine, or another pharmaceutically acceptable salt thereof.

6. The method according to claim 2 which is N,N-dimethyl-N-(2,3-dihydroxypropyl)-N-[$N_1$-(5-methyl-2,4-dioxopyrimidinyl)methoxyethyl]ammonium iodide, or another pharmaceutically acceptable salt thereof.

7. The method according to claim 2 which is N,N-dimethyl-N-(3-hydroxypropyl)-N-[$N_1$-(5-methyl-2,4-dioxopyrimidinyl)methoxyethyl]ammonium iodide, or another pharmaceutically acceptable salt thereof.

8. The method according to claim 2 which is N,N-dimethyl-N-(2-hydroxyethyl)-N-[$N^1$-(5-methyl-2,4)-dioxopyrimidinyl)methoxyethyl]ammonium iodide, or another pharmaceutically acceptable salt thereof.

9. The method according to claim 2 which is N,N-dimethyl-N-3-(hexadecanoyloxy)propyl)-N-dioxopyrimidinyl)methoxyethyl]ammonium iodide, or another pharmaceutically acceptable salt thereof.

10. A method according to claim 1 wherein R is a group of the formula

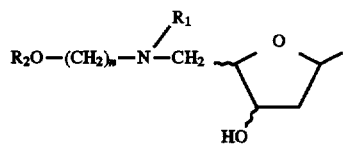

wherein n is 2–6, and the wavy lines indicate either stereochemical configuration;

$R_1$ is one or two lower alkyl groups with the proviso that when two lower alkyl groups are present, then the nitrogen atom is quaternized;

$R_2$ is hydrogen or an alkanoyl group of 1–20 carbon atoms; and their pharmaceutically acceptable salts.

11. The method according to claim 1 wherein the mammal under treatment is afflicted with septic shock.

12. The method according to claim 1 wherein the mammal under treatment is afflicted with cachexia.

13. The method according to claim 1 wherein the mammal under treatment is afflicted with rheumatoid arthritis.

14. The method according to claim 1 wherein the mammal under treatment is afflicted with inflammatory bowel disease.

15. The method according to claim 1 wherein the mammal under treatment is afflicted with multiple sclerosis.

16. The method according to claim 1 wherein the mammal under treatment is afflicted with AIDS.

17. The method according to claim 1 wherein the mammal under treatment is afflicted with Alzheimer's Disease.

18. The method according to claim 1 wherein the inflammatory cytokine being inhibited is tumor necrosis factor (TNF).

19. The method according to claim 18 wherein the mammal under treatment is afflicted with septic shock.

20. The method according to claim 18 wherein the mammal under treatment is afflicted with cachexia.

21. The method according to claim 18 wherein the mammal under treatment is afflicted with rheumatoid arthritis.

22. The method according to claim 18 wherein the mammal under treatment is afflicted with inflammatory bowel disease.

23. The method according to claim 18 wherein the mammal under treatment is afflicted with multiple sclerosis.

24. The method according to claim 18 wherein the mammal under treatment is afflicted with AIDS.

25. The method according to claim 18 wherein the mammal under treatment is afflicted with Alzheimer's Disease.

* * * * *